United States Patent [19]
McEwen et al.

[11] Patent Number: 6,080,166
[45] Date of Patent: Jun. 27, 2000

[54] DIRECT LINEAR DRIVE DERMATOME

[76] Inventors: James Allen McEwen, 10551 Bamberton Drive, Richmond, B.C., Canada, V7A 1K6; Geoffrey Fletcher Auchinleck, Suite 302 - 1233 Beach Avenue, Vancouver, B.C., Canada, V6E 1V4

[21] Appl. No.: 08/799,470

[22] Filed: Feb. 13, 1997

Related U.S. Application Data

[63] Continuation of application No. 08/567,526, Dec. 5, 1995, abandoned.

[51] Int. Cl.$^7$ ..................................................... A61B 17/50
[52] U.S. Cl. ......................... 606/132; 606/131; 606/167; 606/169; 606/172
[58] Field of Search ..................................... 601/131, 132, 601/167, 168, 169, 171, 172, 173

[56] References Cited

U.S. PATENT DOCUMENTS

| | | |
|---|---|---|
| 1,935,605 | 11/1933 | Altruda . |
| 2,691,377 | 10/1954 | Hood . |
| 3,583,403 | 6/1971 | Pohl et al. ............................... 606/132 |
| 4,211,232 | 7/1980 | Mormann et al. .................... 128/305.5 |
| 4,240,432 | 12/1980 | Mormann et al. .................... 128/305.5 |

*Primary Examiner*—Michael A. Brown
*Assistant Examiner*—Benjamin K. Koo
*Attorney, Agent, or Firm*—ipsolon LLP

[57] ABSTRACT

A dermatome for improved cutting of tissue comprises: a blade assembly, including a blade and a blade carrier; a rotational drive assembly; and a housing which engages the blade assembly to constrain the movement of any point on the blade assembly to bidirectional linear movement over a predefined linear range, wherein the engaged blade assembly forms a cover for the housing so that the housing in combination with the engaged blade assembly defines a closed space which surrounds the rotational drive assembly while the blade assembly moves over the predefined linear range. The entire blade assembly may be releasable from the housing, or the blade may be releasable from the blade carrier which remains non-releasably engaged with the housing.

4 Claims, 4 Drawing Sheets

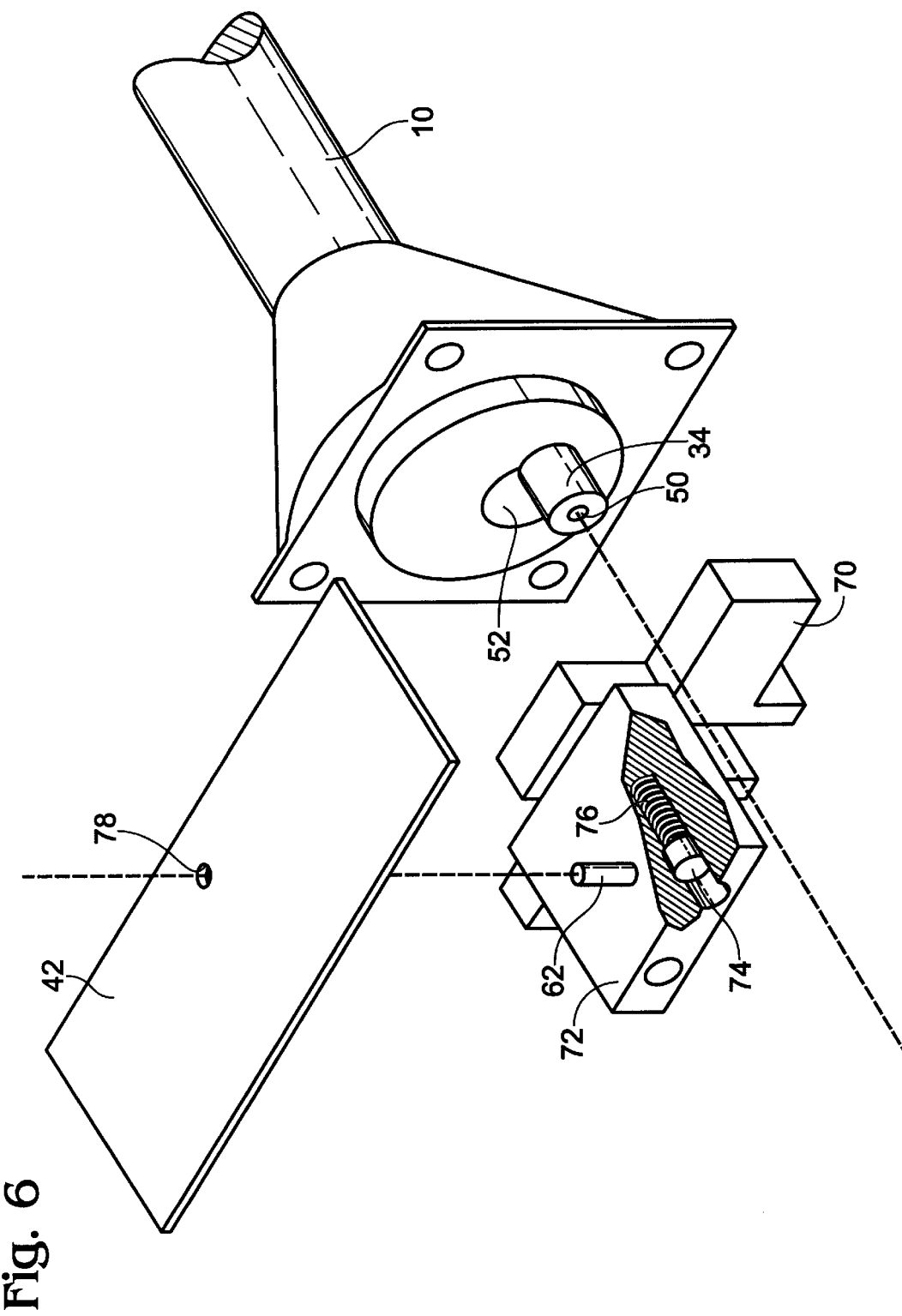

DIRECT LINEAR DRIVE DERMATOME

This application is a continuation of application Ser. No. 08/567,526, filed on Dec. 5, 1995, now abandoned.

FIELD OF THE INVENTION

The present invention relates to a motorized dermatome for cutting thin sections of skin tissue from surgical patients or cadavers, for use in surgical skin grafting procedures. Specifically, the invention provides means for substantially improving the quality of tissue cutting, while at the same time providing significantly longer blade life and an enclosed housing for improved cleaning and sterilization of the dermatome, and improved blade replacement.

BACKGROUND OF THE INVENTION

Many motorized dermatomes are known in the prior art. Typical examples are described in U.S. Pat. No. 2,419,114 (Briegel), U.S. Pat. No. 2,457,772 (Brown), U.S. Pat. No. 2,787,272 (Groom), U.S. Pat. No. 3,412,732 (Simon), U.S. Pat. No. 3,428,045 (Kratzsch), U.S. Pat. No. 3,670,734 (Hardy), U.S. Pat. No. 3,820,543 (Vanjushin), and U.S. Pat. No. 4,917,086 (Feltovich). All of these devices are fundamentally similar, in that a sharp blade edge is placed in contact with skin and driven by the motor in an oscillatory fashion to create a sawing action. In order to move the blade edge back and forth, the rotational action of the drive motor is converted to more or less linear motion through the use of a number of linkages. A means is usually provided for permitting the blade to cut the skin to a pre-selected depth so that a thin layer of skin can be removed as the dermatome is moved forward.

The cutting characteristics of the dermatome are determined by the motion of the cutting blade. The quality of the cut, and the ease with which a dermatome can be moved forward as skin is cut, is related to the amplitude of the oscillating motion of the blade. At low amplitude, the skin being cut is able to stretch slightly from side to side, preventing any significant relative motion between the blade and the skin. As the amplitude of the blade oscillation increases, this elastic deformation of the skin is overcome and the blade begins to cut through the skin. During each sweep of the blade a certain part of the blade motion is wasted in overcoming this elastic deformation before cutting resumes. When the amplitude of the blade motion is much larger than the amount of motion required to overcome the elastic deformation, the blade provides a significant amount of cutting action on each sweep. As the skin must be cut free of underlying layers for the dermatome to be moved forward, increased amplitude of oscillation permits more rapid advancing of the dermatome and more rapid removal of the skin graft. As the amplitude of oscillation of the blade increases, the size of the dermatome increases. Therefore, there is an optimum balance between the amplitude of oscillation and the physical size of the dermatome.

Sharpness of the blade edge is another major factor affecting the quality of tissue cutting and the characteristics of a dermatome. Most dermatomes provide a means for quickly replacing a dull blade during skin grafting surgery in recognition of the fact that blades quickly lose their sharpness. Despite similarities in the materials and process of manufacture of these blades, some dermatomes seem subjectively to remain sharper much longer than others. Loss of sharpness and wearing of the blade is primarily due to the motion of the blade against the tissue.

When a blade is cutting tissue, the only useful motion is purely linear. The sawing action of the blade along the axis of the blade edge provides the cutting action while the dermatome is moved forward against the skin to bring more tissue to bear on the blade edge. Any other motion of the blade contributes only to dulling the blade. If the blade is permitted to yaw about an axis perpendicular to the blade edge during its oscillation, the blade edge will be repeatedly pressed into the tissue and withdrawn from tissue during each cycle, having the effect of "hammering" the edge of the blade into a flatter and less sharp shape. If the blade pitches up and down in a direction perpendicular to the direction of the movement of the blade forward along the skin, the blade will be repeatedly scraped across the tissue, having an effect equivalent to "filing" the edge of the blade into a flatter and less sharp shape.

Quality of cutting and maintenance of blade sharpness are only two of the factors having a major effect on the performance and ease of use of a dermatome. Another factor of major importance relates to the cleaning of a dermatome between uses, because an improperly or incompletely cleaned dermatome cannot be satisfactorily re-sterilized for reuse. The time, labor-intensivenss and resulting quality of cleaning are important aspects of dermatome use and re-use. When a dermatome is used to cut and remove skin, a considerable amount of tissue, debris and other materials will come into contact with the dermatome. As the dermatome must be rigorously cleaned and then re-sterilized between uses, is desirable that there be no opening in the external surface of the dermatome which allows tissue to come into contact with internal components of the drive mechanism of the dermatome, and which may allow tissue to become entrapped by the internal components of the drive mechanism of the dermatome. However, no dermatome known in the art provides a housing to enclose the internal components of the drive mechanism, which typically converts the rotational motion of a drive source into a more or less linear motion to drive the blade, while at the same time providing means for quickly and easily removing and replacing blades during usage. As a result, cleaning of prior art dermatomes typically requires removal of tissue and debris from the internal region of the dermatome surrounding components of the drive mechanism; such cleaning is very time-consuming and imperfect, resulting in increased labor costs and reduced quality associated with dermatome usage.

An ideal dermatome would provide a relatively large (⅜ inch or more) amplitude of blade oscillation along a perfectly linear path defined by the edge of the blade, while preventing any other motions of the blade with respect to the rest of the dermatome. The motor and all linkages forming the drive mechanism would be contained within a housing having no open space which would allow the entry of tissue and debris into the region of the drive mechanism, and the dermatome would at the same time include a means for quickly and easily replacing blades during surgery. The number of linkages between the motor drive and the blade, and the number of moving parts, would be minimized to improve the efficiency and reliability of the dermatome. Ideally, the rotational motion of a motor assembly in a powered dermatome should directly drive a blade assembly in purely linear motion, with no additional linkages having non-rotational, arcuate or non-linear motions between the motor assembly and blade assembly.

Dermatomes described in the prior art have included a number of attempts to implement and combine these desirable features. Brown (U.S. Pat. No. 2,457,772), Groom (U.S. Pat. No. 2,787,272), Simon (U.S. Pat. No. 3,412,732), Kratzsch (U.S. Pat. No. 3,428,045) and Vanjushin (U.S. Pat.

No. 3,820,543) all show guide rods intended to limit the motion of a blade carrier to linear motion along a defined axis, to which the blade is attached. These prior-art devices include drive mechanisms which provide accurate translation of the rotational motion of the shaft of a motor into a linear motion of a blade carrier, but none includes means to assure that the dermatome blade engages the blade carrier such that the axis of linear motion of the blade carrier is exactly parallel to the axis of the blade edge. In addition, none of these prior-art dermatomes provides a housing which encloses and surrounds the drive mechanism to prevent the entry of tissue, skin lubricant, and other debris while at the same time permitting quick and easy blade replacement during usage.

The Padgett Dermatome (Padgett Instruments, Kansas) provides for linear motion of the blade by guiding the back edge of the blade against two steel pins, while constraining the blade from pitching motion by guiding it between the dermatome body and a removable width plate. Motion is imparted to the blade by a yoke which pivots on a fixed pin. The yoke, when driven by the motor, swings through a portion of an arc. A pin on the yoke fits into a hole in the blade, while a spring in the yoke holds the blade against the guide pins. Friction and vibration are generated, and efficiency is lost, in the linkage because the rotary motion of the motor is first converted into arcuate motion, and then into linear motion at the blade. This dermatome, while providing excellent linear blade motion, provides reasonably large amplitude blade motion through the use of a very large motor and head, which makes the device unwieldy. In addition, an open space in the dermatome head which enables the yoke pin to engage the blade also enables tissue, skin lubricant, and other debris to enter into the dermatome head and into the region surrounding the yoke and drive mechanism.

The Feltovich dermatome (U.S. Pat. No. 4,917,086) is very similar to the Padgett dermatome, but has a blade assembly comprised of a metal blade non-releasably attached to a thermoplastic blade carrier. The Feltovich dermatome does not include steel guide pins, as included in the Padgett dermatome, to keep the motion of the blade assembly purely linear. Although a smaller and lighter dermatome body and motor make the device easier to handle, the very small amplitude of motion of the blade assembly, as well as the significant non-linearity of motion of the blade assembly, result in a relatively poorer quality of cut, less cutting efficiency, and shorter blade life, for the reasons described above. Also, like the Padgett dermatome, the Feltovich dermatome has an indirect drive, with a yoke component between the motor and the blade assembly which describes an arcuate motion. The arcuate motion of the yoke component generates friction between the yoke and blade assembly, further reducing cutting efficiency, and produces vibration. Also, the motion of the yoke requires an open space in the dermatome head to enable a pin at the end of the yoke to engage the blade assembly, and this open space also enables tissue, skin lubricant, and other debris to enter into the dermatome head and into the region surrounding the yoke and drive mechanism of the Feltovich dermatome.

SUMMARY OF THE INVENTION

The present invention provides a dermatome for cutting skin tissue in an improved manner by driving a blade assembly in a linear motion directly from a rotational drive assembly, thus substantially reducing non-linear motion of the blade assembly and producing blade motion over a greater bidirectional linear range while maintaining a dermatome body of clinically acceptable size. The invention comprises: a blade assembly, including a blade and a blade carrier; a rotational drive assembly; and a housing which engages the blade assembly to constrain the movement of any point on the blade assembly to bi-directional linear movement over a predefined linear range, wherein the engaged blade assembly forms a cover for the housing so that the housing in combination with the engaged blade assembly defines a closed space which surrounds the rotational drive assembly while the blade assembly moves over the predefined linear range. The invention may be constructed so that the entire blade assembly is be releasable from the housing, or so that the blade is releasable from the blade carrier which remains non-releasably engaged with the housing.

BRIEF DESCRIPTION OF THE DRAWINGS

FIG. 6 is an exploded view showing the moving parts of the dermatome of FIG. 5, with the enclosure not shown for clarity.

DESCRIPTION OF THE SPECIFIC EMBODIMENT

Figure 1:
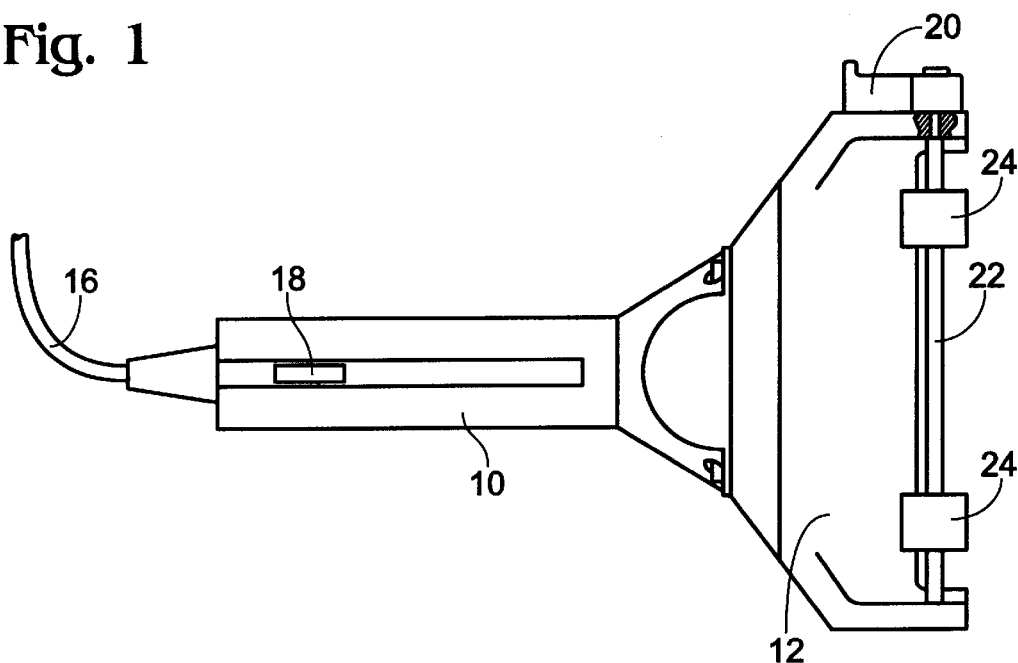
FIG. 1 is a top view of a dermatome according to the invention.

Referring to FIG. 1, the specific embodiment of the dermatome according to the invention is composed of a handle 10, connected to a head 12. Handle 10 encloses motor 14 (not shown in FIG. 1), which is connected to a source of power by cable 16. Switch 18 enables the user to turn on and off motor 14 while operating the dermatome. Head 12 forms part of a housing to enclose the drive mechanism of the dermatome as hereinafter described. Thickness adjustment lever 20 rotates eccentrically mounted shaft 22, which varies the position of bushing 24.

Figure 2:
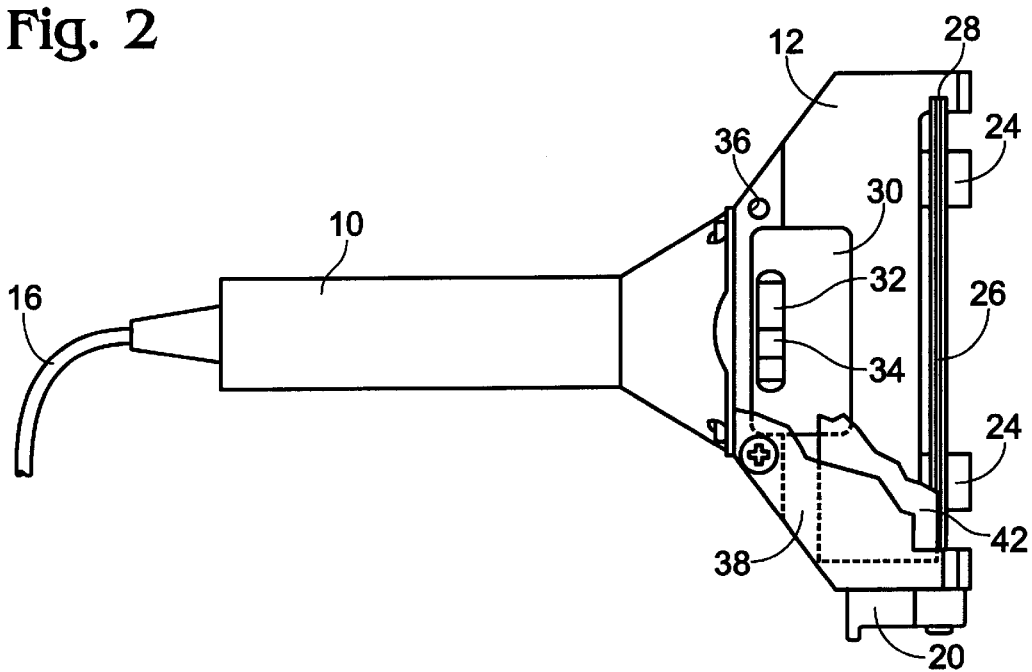
FIG. 2 is a bottom view of the dermatome of FIG. 1 with the blade and width plate shown in partial cutaway for clarity.

Referring to FIG. 2, bushings 24 are connected to thickness guide 26, which is constrained to move within slots 28. Rotation of thickness adjustment lever 20 causes thickness guide 26 to move within the slots.

Cut into the bottom face of head 12 is recess 30, within which is aperture 32. 5 Aperture 32 provides access to eccentric drive eccentric drive bushing 34. Threaded holes 36 provide a fastening means for width plate 38 (shown in partial cutaway in FIG. 2).

Figure 3:
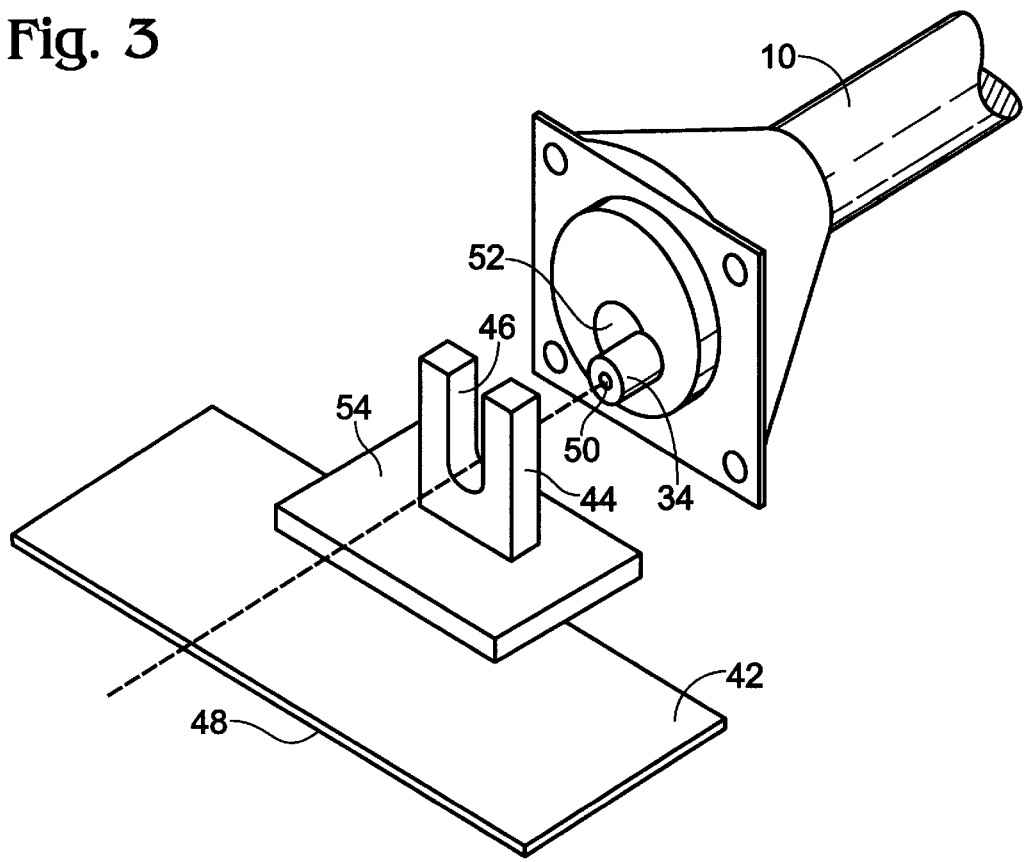
FIG. 3 is an exploded view showing the moving parts of the dermatome of FIG. 1, with the enclosure not shown for clarity.

FIG. 3 shows the blade assembly, which is comprised of blade 42, which in the preferred embodiment is made of stainless steel, sharpened along edge 48, and blade carrier 44. Blade carrier 44 is rigidly and non-releasably attached to blade 42 such that blade 42 and blade carrier 44 comprise one rigid part. Blade carrier 44 may be made of thermoplastic material or a lightweight metal such as aluminum, and may be cast, molded or otherwise formed onto blade 42. Blade carrier 44 includes a drive slot 46 which is disposed to fit over eccentric drive bushing 34, and cover plate 54, which is shaped and sized to fit within recess 30 in head 12 so that cover plate 54 in combination with recess 30 constrains the blade assembly to motions only along an axis parallel to aperture 32. Drive slot 46 has a width of ⅜ inch, which is substantially the same as the diameter of eccentric drive bushing 34.

Eccentric drive bushing 34 is rotatably attached to shaft 50 on an axis parallel to, but displaced from, the axis of shaft 52 of motor 14 (not shown in FIG. 3) by a predetermined distance of approximately 3/16 inch, such that operation of motor 14 causes eccentric rotation of eccentric drive bushing 34. When assembled for use, the blade assembly is placed into head 12 such that blade carrier 44 fits into recess 30 and drive slot 46 engages eccentric drive bushing 34 through aperture 32.

Figure 4:
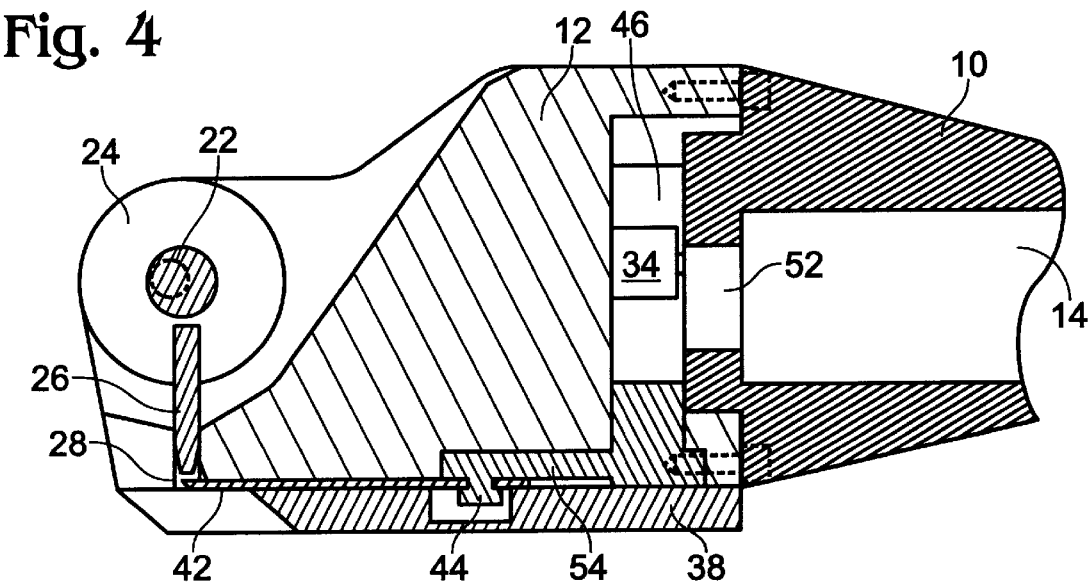
FIG. 4 is a cross section view of the dermatome of FIG. 1.

FIG. 4 shows a cross section of dermatome head 12 as it would be assembled for use. After the blade assembly is fitted into head 12, width plate 38 is fastened to head 12 using screws inserted into threaded holes 36.

When switch 18 is used to activate motor 14, eccentric drive bushing 34 moves within drive slot 46 of blade carrier 44 to move the blade assembly. Cover plate 54 of the blade assembly limits the motion of the blade assembly to linear, oscillatory motion because cover plate 54 is constrained to move within recess 30. In this way, in the specific embodiment the rotational motion of motor 14 is directly converted to purely linear motion of the blade assembly, with negligible yawing and pitching motions, which have produced unnecessary "hammering" and "filing" of the blade edge and premature dulling of the blade edge, as well as producing unnecessary vibration, in prior-art dermatomes as described above. Also, because the predetermined eccentric axis displacement distance is 3/16 inch in the specific embodiment, the resulting linear displacement range is ⅜ inch; thus, in contrast to prior-art dermatomes, a large amplitude of linear blade oscillation is achieved by the direct linear drive within a dermatome body having a small, clinically acceptable size; this results in improved dermatome performance, as described above.

In the specific embodiment, cover plate 54 of blade carrier 44 is sized to ensure that aperture 32 is entirely covered by cover plate 54 throughout the full range of motion of cover plate 54 during rotation of eccentric drive bushing 34. In this way, cover plate 54 provides the dual functions of both guiding the motion of the blade assembly, and forming a housing in combination with head 12 which covers aperture 32, and completely encloses the rotational drive assembly over the entire linear range of motion of blade 42, thus preventing the entry of tissue, skin lubricant, and other debris into the interior region of head 12.

In the blade assembly of the specific embodiment, blade 42 is formed from stainless steel and blade carrier 44 is formed from inexpensive thermoplastic material non-releasably attached to blade 42, making it cost-effective to remove and discard the blade assembly after use on individual patients or cadavers, thus eliminating the need to clean and re-sterilize the blade assembly.

Description of the Alternate Embodiment

Figure 5:
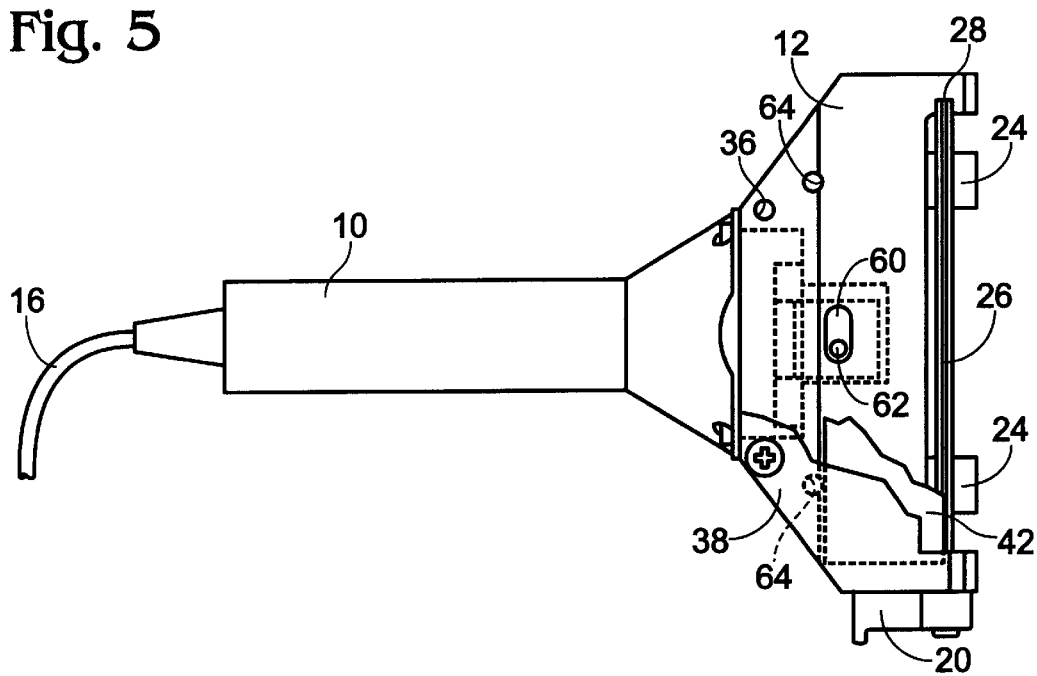
FIG. 5 is a bottom view of an alternate embodiment of a dermatome according to the invention.

FIG. 5 shows an alternate embodiment of a dermatome according to the invention. In the alternate embodiment, provision is made for conveniently removing and replacing the dermatome blade while at the same time maintaining a housing around the drive mechanism in the dermatome head to prevent the entry of tissue, lubricant and other debris into the interior region of the dermatome head around the drive mechanism.

As can be seen in FIGS. 5 and 6, protruding from opening 60 on the bottom face of head 12 is blade drive pin 62. Blade drive pin 62 is affixed to blade carrier tab 72, which covers opening 60 and forms part of a housing surrounding the drive mechanism in head 12 over the full range of motion of blade drive pin 62. The drive mechanism within head 12 as hereinafter described causes blade drive pin 62 to move within opening 60 over a predefined linear range of approximately ⅜ inch. Guide pins 64 shown in FIG. 5 provide a means for helping to constrain the motion of blade 42 (shown in partial cutaway in FIG. 5) to linear motion only. Threaded holes 36 receive two screws which hold width plate 38 (shown in partial cutaway in FIG. 5) in place during use of the dermatome.

FIG. 6 shows the mechanism contained within head 12 of the alternate embodiment and its relationship with motor 14 contained within handle 10. In the alternate embodiment, eccentric drive bushing 34 fits into drive slot 68 of blade carrier guide bar 70. Blade carrier guide bar 70 is constrained to move within a guide slot cut into head 12. Connected to blade carrier guide bar 70 is blade carrier tab 72. Blade carrier tab 72 is mounted to blade carrier guide bar 70 with screws 74 and springs 76 (one shown in FIG. 6). Springs 76 act on blade carrier tab 72 to push it toward blade carrier guide bar 70, while permitting blade carrier tab 72 to be moved away from blade carrier guide bar 70 along the axes of screws 74.

Affixed to the top of blade carrier tab 72 is blade drive pin 62, which fits into drive hole 78 of blade 42. During operation, motor 14 rotates shaft 52, which in turn drives eccentric drive bushing 34. Eccentric drive bushing 34 drives blade carrier guide bar 70 from side to side. Thus rotational motion of motor 14 is translated into linear motion of blade carrier guide bar 70, and this linear motion is transferred by blade carrier tab 72 to blade drive pin 62 and thus to blade 42. In this way, the rotational motion of motor 14 is directly converted to linear motion of blade 42, with negligible yawing and pitching motions which have produced unnecessary "hammering" and "filing" of the blade edge and premature dulling of the blade edge, as well as producing unnecessary vibration, in prior-art dermatomes as described above.

The maximum amplitude of the side to side motion of blade 42 is equal to twice the predetermined displacement distance between the axis of shaft 52 and the axis of eccentric drive bushing 34. In the alternate embodiment, the predetermined displacement distance is 3/16 inch, and thus the maximum amplitude of the bidirectional linear movement of blade 42 is ⅜ inch. As in the specific embodiment, the alternate embodiment is an improvement over prior-art dermatomes in that it achieves a relatively large and clinically desirable maximum amplitude of linear motion of blade 42 using a direct linear drive mechanism housed and enclosed within a relatively small dermatome head 12.

Figure 7:
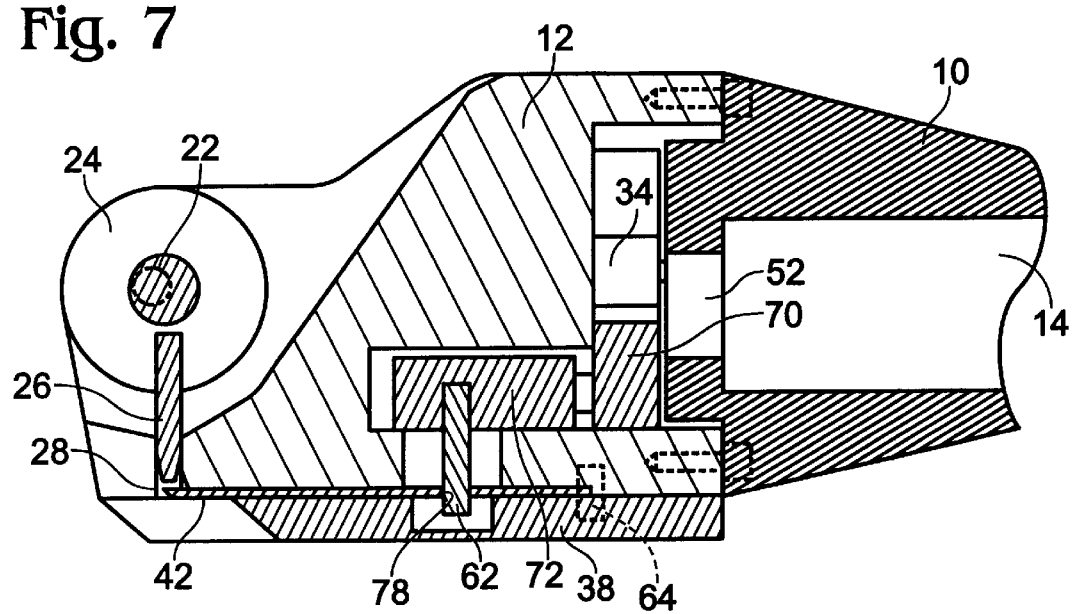
FIG. 7 is a cross section view of the dermatome of FIG. 5.

FIG. 7 shows how the components of FIG. 6 are contained within head 12. Blade carrier tab 72 functions as a cover for opening 60 such that blade carrier tab 72 and housing 12 enclose the components of the drive mechanism of the dermatome over the full linear range of motion of blade carrier tab 72.

To use the alternate embodiment of the dermatome, width plate 38 is removed from the bottom of the dermatome, by removing the screws in threaded holes 36. A new blade 42 is placed into the dermatome so that drive pin 62 fits into drive hole 78. Blade 42 is then moved forward against the spring tension provided by springs 76 against blade carrier tab 72, until the back edge of blade 42 fits in front of guide pins 64. Width plate 38 is then replaced over blade 42 and screwed into place. To remove blade 42, the procedure is reversed so that drive hole 78 of blade 42 can be disengaged from drive pin 62. In the alternate embodiment, only blade 42 need be replaced or discarded, while blade carrier guide bar 70 and blade carrier tab 72 remain engaged with head 12 as described above. Blade 42 may be formed of metal, or a combination of metal and plastic non-releasably bonded to the metal to reduce costs.

Typical Use

As shown in FIGS. 4 and 7, when either the specific embodiment or the alternate embodiment of the dermatome is assembled, the front edge of blade 42 is directly below thickness guide 26. The user may now rotate thickness adjustment lever 20 to adjust the space between the edge of blade 36 and thickness guide 26 until the desired skin graft thickness is set.

To use the dermatome, the edge of blade 42 is placed in contact with the donor tissue, switch 18 is activated and the dermatome is moved forward. The oscillation of blade 42 cuts a thin layer of tissue which is lifted over the top of blade 42 and may be removed.

Many modifications and variations of the mechanisms described are possible without departing from the principles of the invention, therefore the invention should be limited only by the scope of the appended claims.

We claim:

1. A dermatome for cutting tissue comprising:
   a blade having a drive hole formed therein;
   a blade carrier having:
      attachment means for releasably attaching the blade to the blade carrier;
      drive pin means for engaging the drive hole with a pin member for transferring motion of the blade carrier to the blade, and
      the blade carrier having a concave surface that is continuous with two substantially parallel sides that are spaced apart by a predetermined carrier distance;
   a rotational drive assembly comprising
      a shaft having a substantially cylindrical shape and a shaft axis around which the shaft rotates, and
      an eccentric component attached to the shaft having a substantially cylindrical shape, a predetermined cylindrical diameter and an eccentric component axis aligned parallel to the shaft axis but displaced from the shaft axis by a predetermined eccentric distance, wherein the eccentric component engages the concave surface of the blade assembly and rotates around the eccentric component axis when the shaft rotates, and wherein the predetermined cylindrical diameter is substantially equivalent to the predetermined carrier distance; and
   a housing which engages the blade carrier to constrain the movement of any point on the blade carrier to bidirectional linear movement wherein the housing is adapted to define a space surrounding the rotational drive assembly, wherein the housing is further adapted so that the space surrounding the rotational drive assembly is enclosed as a result of the engagement of the housing and the blade carrier, and wherein
   the blade carrier and the housing are further adapted so that the blade is attachable to the blade carrier while the enclosed space surrounding the rotational drive assembly is maintained by the housing in combination with the engaged blade carrier.

2. A dermatome as described in claim 1 wherein the blade is formed of metal having a straight edge shaped to cut tissue along the straight edge.

3. A dermatome as described in claim 2 wherein the blade includes thermoplastic material non-releasably attached to the metal.

4. A dermatome for cutting tissue comprising:
   a blade having a drive hole formed therein;
   a linear drive means which moves a blade carrier in bidirectional linear motion through a predetermined distance along an axis, the blade carrier including:
      attachment means for releasably attaching the blade to the blade carrier and
      a drive pin for engaging the hole in the blade, and
      a sealing surface oriented parallel to the axis; and
   a housing adapted to engage the sealing surface so that the housing in combination with the blade carrier defines a closed space which surrounds the linear drive means while the blade carrier moves over the predetermined distance, wherein the housing is further adapted to engage the sealing surface so that the blade is attachable to the blade carrier while the closed space surrounding the rotational drive assembly is maintained.

* * * * *